United States Patent [19]

Hammond et al.

[11] Patent Number: 5,432,080
[45] Date of Patent: Jul. 11, 1995

[54] DNA ENCODING VARIANTS OF HUMAN CORTICOSTEROID BINDING GLOBULIN

[75] Inventors: Geoffrey L. Hammond, Lambeth; George V. Avvakumov, London, both of Canada

[73] Assignee: Allelix Biopharmaceuticals Inc., Mississauga, Canada

[21] Appl. No.: 994,423

[22] Filed: Dec. 16, 1992

[51] Int. Cl.$^6$ .................. C12N 5/10; C12N 15/00
[52] U.S. Cl. .................. 435/252.3; 536/23.5; 530/386
[58] Field of Search .................. 536/23.5; 435/252.3; 530/386

[56] References Cited

U.S. PATENT DOCUMENTS 4,997,814  3/1991  Hammond .................. 514/8
5,086,039  2/1992  Hammond .................. 514/8

OTHER PUBLICATIONS

Akhrem et al., "Structural Organization Of The Carbohydrate Moiety Of Human Transcortin As Determined By Methylation Analysis Of The Whole Glycoprotein", Biochimica et Biophysica Acta, 1982, pp. 177–180.

Hossner et al., "Plasma Clearance and Organ Distribution Of Native And Desialylated Rat And Human Transcortin: Species Specificity", Endocrinology, 1981, vol. 8, pp. 1780–1786.

Ghose-Dastidar et al., "Expression of Biologically Active Human Corticosteroid Binding Globulin By Insect Cells: Acquistion of function Requires Glycosylation And Transport", Proc. Natl. Acad. Sci., Aug. 1991, vol. 88, pp. 6408–6412.

Rosner, "The Function Of Corticosteroid-Binding Globulin and Sex Hormone-Binding Globulin: Recent Advances", Endocrine Revviews, 1990, vol. 11 No. 1, pp. 80–91.

Strel'Chyonok et al., "Interaction of Human CBG With Cell Membranes", J. Steroid Biochem Molec Biol., 1991, vol. 40, pp. 795–803.

Mikelson et al., "Steroid-Protein Interactions. Human Corticosteroid-Binding Globulin: Characterization Of Dimer And Electrophoretic Varients", Biochemistry, 1982, vol. 21, pp. 654–660.

Kunkel et al., "Rapid And Efficient Site-Specific Mutagenesis Without Phenotypic Selection", Proc. Natl. Acad. Sci., Jan. 1985, pp. 488–492.

Barnett, et al., "Rapid Generation Of DNA Fragments By PCR: Amplification Of Crude, Synthetic Oligonucleotides", Nucl. Acids Research, 1990, vol. 18, No. 10, p. 3094.

Wosnick et al., "Total Chemical Synthesis And Expression in *Escherichia Coli* Of A Maize Glutahione–Transferase (GST) Gene", Gene, 76, 1989, pp. 153–160.

Rosner, "Recent Studies On The Binding Of Cortisol in Serum", Journal Of Steroid Biochemistry, 1972, vol. 3, pp. 531–542.

Robinson et al., "A Solid–Phase Radioimmunoassay For Human Corticosteroid Binding Globulin", Journal Of Endocrinology Ltd., 1985, 104, pp. 259–267.

Mickelson et al., "d–Protein Interactions. Human Corticosteroid Binding Globulin: Physicochemical Properties And Binding Specificity", Biochemistry, 1981, 20, pp. 6211–6218.

Hammond et al., "Primary Structure Of Human Corticosteroid Binding Globulin, Deduced From Hepatic And Pulmonary cDNAs, Exhibits Homology With Serin Protease Inhibitors", Proc. Natl. Acad. Sci., Aug. 1987, vol. 84, pp. 5153–5157.

Sanger et al., "DNA Sequencing With Chain–Terminating Inhibitors", Proc. Natl. Acad. Sci., Dec. 1977, vol. 74, No. 12, pp. 5463–5467.

Laemmli, "Cleavage Of Structural Proteins During The Assembly Of The Head Of Bacteriophage T4", Nature (London), Aug. 15, 1970, vol. 227, pp. 680–685.

Hammond et al., "A Versatile Method For The Determination Of Serum Cortisol Binding Globulin And Set Hormone Binding Globulin Binding Capacities", Clinics Chimca Acta, 132, 1983, pp. 101–110.

*Primary Examiner*—Robert A. Wax
*Assistant Examiner*—Keith D. Hendricks
*Attorney, Agent, or Firm*—Foley & Lardner

[57] ABSTRACT

A novel steroid-binding variant of human corticosteroid binding globulin in which one or more of the glycosylation sites, other than the glycosylation site at amino acid position 238, has been functionally disrupted is complexed with an anti-inflammatory ligand in the treatment of inflammation in mammals.

7 Claims, 6 Drawing Sheets

FIG. 1a

```
                                                         CAG CCT ACC GCA GAC TGG CTA TAC TGG ACA    35

-22 Met Pro Leu Leu Leu Tyr Thr Cys Leu Leu Trp Leu Pro Thr Ser Gly Leu Trp Thr Val    95
    ATG CCA CTC CTC CTG TAC ACC TGT CTT CTC TGG CTG CCC ACC AGC GGC CTC TGG ACC GTC

-2 Gln Ala Met Asp Pro Asn Ala Ala Tyr Val •Asn Met Ser Asn His Arg Gly Leu Ala   155
    CAG GCC ATG GAT CCT AAC GCT GCT TAT GTG AAC ATG AGT AAC CAT CGG GGC CTG GCT
         ─── NcoI ───

19 Ser Ala Asn Val Asp Phe Ala Phe Ser Leu Tyr Lys His Leu Val Ala Leu Ser Pro Lys   215
    TCA GCC AAC GTT GAC TTT GCC TTC AGC CTG TAT AAG CAC CTA GTG GCC TTG AGT CCC AAA

39 Lys Asn Ile Phe Ile Ser Pro Val Ser Ile Ser Met Ala Leu Ala Met Leu Ser Leu Gly   275
    AAG AAC ATT TTC ATC TCC CCT GTG AGC ATC AGC ATG GCC CTA GCT ATG CTG TCC CTG GGC
                                                 ─── NcoI ───

59 Thr Cys Gly His Thr Arg Ala Gln Leu Leu Gln Leu Leu Gly Phe •Asn Leu Thr Glu Arg   335
    ACC TGT GGC CAC ACA CGG GCC CAG CTC CTC CAG CTG CTG GGT TTC AAC CTC ACT GAG AGG
                                                              ───────

79 Ser Glu Thr Glu Ile Met Thr Met Gly Asn Ala Leu Phe Leu His Gln Leu Asp Ser Asp   395
    TCT GAG ACT GAA ATG ACT ATG GGC AAT GCC CTC TTT CTT CAT CAA CTG GAC TCA GAC

99 Thr Ser Leu Glu Leu Phe Ser Ala Asp Ile Lys His Tyr Tyr Glu Ser Glu Val Leu Leu   455
    ACC AGC CTA GAA CTG TTT TCA GCA GAC ATC AAG CAC TAC TAT GAG TCA GAG CTG CTG

119 Glu Ser Phe Ser Ala Asp Thr Asn Ala Leu Tyr Tyr Glu Val Ser Gly Val Leu Ala Met Asn Phe   515
    GAG AGC TTC AGC GCA GAC ACA GCC CTT GCC AAT TAC GAG GTC TCA GGC GTC TTG GCT ATG AAT TTC

139 Gln Asp Trp Ala Thr Ala Ser Arg Gln Ile Asn Ser Tyr Val Lys •Asn Lys Thr Gln Gly   575
    CAG GAC TGG GCA ACA GCC AGC AGA CAG ATC AAC AGC TAT GTC AAG AAT AAG ACA CAG GGG

159 Lys Ile Val Asp Leu Phe Ser Gly Leu Asp Ser Pro Ala Ile Leu Val Leu Val Asn Tyr   635
    AAA ATT GTC GAC TTG TTT TCA GGG CTG GAT AGC CCA GCC ATC CTC GTC CTG GTC AAC TAT

179 Ile Phe Phe Lys Gly Thr Trp Thr Gln Pro Phe Asp Leu Ala Ser Thr Arg Glu Glu Asn   695
    ATC TTC TTC AAA GGC ACA TGG ACA CAG CCC TTT GAC CTG GCA AGC ACC AGG GAG GAG AAC
```

FIG. 1b

```
199 Phe Tyr Val Asp Glu Thr Thr Val Lys Val Pro Met Met Leu Gln Ser Ser Thr Ile      755
    TTC TAT GTG GAC GAG ACA ACT GTG AAG GTG CCC ATG ATG TTG CAG TCG AGC ACC ATC

219 Ser Tyr Leu His Asp Ser Glu Leu Pro Cys Gln Leu Val Gln Met Asn Tyr Val Gly •Asn  815
    AGT TAC CTT CAT GAC TCA GAG CTC CCC TGC CAG CTG GTG CAG ATG AAC TAC GTG GGC  AAT

239 Gly Thr Val Phe Phe Ile Leu Pro Asp Lys Gly Lys Met Asn Thr Val Ile Ala Leu      875
    GGG ACT GTC TTC TTC ATC CTT CCG GAC AAG GGG AAG ATG AAC ACA GTC ATC GCT GCA CTG

259 Ser Arg Asp Thr Ile Asn Arg Trp Ser Ala Gly Leu Thr Ser Gln Val Asp Leu Tyr      935
    AGC CGG GAC ACG ATT AAC AGG TGG TCC GCA GGC CTG ACC AGC CAG GTG GAC CTG TAC

279 Ile Pro Lys Val Thr Ile Ser Gly Val Tyr Asp Leu Gly Asp Val Leu Glu Met Gly      995
    ATT CCA AAG GTC ACC ATC TCT GGA GTC TAT GAC CTT GGA GAT GTG CTG GAG ATG GGC

299 Ile Ala Asp Leu Phe Thr Asn Gln Ala •Asn Phe Ser Arg Ile Thr Gln Asp Ala Gln Leu  1055
    ATT GCA GAC TTG TTC ACC AAC CAG GCA AAT TTC TCA CGC ATC ACC CAG GAC GCC CAG CTG

319 Lys Ser Ser Lys Val Val His Lys Ala Val Leu Gln Leu Asn Glu Glu Gly Val Asp Thr  1115
    AAG TCA TCA AAG GTG CAT AAA GCT GTG CTG CAA CTC AAT GAG GAG GGT GTG GAC ACA

339 Ala Gly Ser Thr Gly Val •Asn Leu Thr Ser Lys Pro Ile Ile Leu Arg Phe Asn          1175
    GCT GGC TCC ACT GGG GTC AAC CTA ACG TCC AAG CCT ATC ATC TTG CGT TTC AAC

359 Gln Pro Phe Ile Met Ile Phe Asp His Phe Thr Trp Ser Ser Leu Phe Leu Ala Arg      1235
    CAG CCC TTC ATC ATG ATC TTC GAC CAC TTC ACC TGG AGC AGC CTT TTC CTG GCG AGG 383
379 Val Met Asn Pro Val ---
    GTT ATG AAC CCA GTG TAA GAGACCACCCCAGAGCCTCAGCACTGTCTGACTTGGGAACCAGGATCCCA       1308

CAGAAATGTTTGGAGAGCGGGAGGTTCCCCCAATCTCCTCCTTCTCCCCTCCAACCAGAGTTGTGTCTAACT             1387

TTAGGCATCTTTTAATAAATGTCATTGCGACTCTGA₃₆                                               1458
```

FIG. 2a

Table 1. Sequences of the mutagenic oligonucleotide primers.

| Mutation | Oligonucleotide |
|---|---|
| Asn$^9$→Gln | GGTTACTCATTG$\underline{C}$ACATAAGCT |
| Asn$^{74}$→Gln | CTCACTGAGTT$\underline{G}$GAAACCCAG |
| Thr$^{76}$→Ala | GACCCTCAGG$\underline{G}$AGGTTGAAA |
| Asn$^{154}$→Gln | CTGTGTCTT$\underline{C}$TT$\underline{G}$CTTGACATA |
| Asn$^{238}$→Gln | GACAGTCCC$\underline{C}$T$\underline{G}$GCCCACGTA |
| Thr$^{240}$→Ala | AAGAAGACAG$\underline{C}$CCCATTGCCC |
| Asn$^{308}$→Gln | GCGTGAGAA$\underline{C}$T$\underline{G}$CCTGGTT |
| Asn$^{347}$→Gln | GGACGTCAG$\underline{T}$TG$\underline{T}$AGGGTGAC |

Altered nucleotides are underlined.

FIG. 2b

| LOCATION OF CONSENSUS SITES FOR N-GLYCOSYLATION IN WILD-TYPE (#1) AND MUTANT PROTEINS (#2-#15) | RELATIVE AMOUNT (%) IN CULTURE MEDIUM |
|---|---|
| 1. N—I(NMS) II(NLT) III(NKT) IV(NGT) V(NFS) VI(NLT)—C | 100 |
| 2. N—QMS NLT NKT NGT NFS NLT—C | 74±15 |
| 3. N—NMS QLT NKT NGT NFS NLT—C | 41±10 |
| 4. N—NMS NLT NLA NGT NFS NLT—C | 69±12 |
| 5. N—NMS NLT NKT QKT NFS NLT—C | 85±2 |
| 6. N—NMS NLT NKT NGT QGT NLT—C | 52±15 |
| 7. N—NMS NLT NKT NGT NFS NGA—C | 45±3 |
| 8. N—NMS NLT NKT NGT QFS NLT—C | 113±18 |
| 9. N—NMS NLT NKT NGT NFS QLT—C | 79±12 |
| 10. N—NMS QLT NKT QGT NFS NLT—C | 58±6 |
| 11. N—NMS NLT NLA NGT NGA NLT—C | 52±7 |
| 12. N—QMS NLT QKT NGT QFS QLT—C | 74±12 |
| 13. N—QMS NLT QKT QGT QFS QLT—C | 74±7 |
| 14. N—QMS NLA QKT NGT QFS QLT—C | 78±2 |
| 15. N—QMS QLT QKT QGT QFS QLT—C | 5±2 |

FIG. 3

| Mutant # | Construction plasmid* | Donor* | Product |
|---|---|---|---|
| 10 | SalI/XbaI-restricted pSelect/CBG mutant #3 | SalI/XbaI fragment of CBG mutant #6 | Mutant #10 (Gln74/Gln238) |
| 11 | SalI/XbaI-restricted pSelect/CBG mutant #4 | SalI/XbaI fragment of CBG mutant #7 | Mutant #11 (Ala76/Ala240) |
| 12 A. | HindIII/StuI-restricted pSelect/CBG mutant #9 | HindIII/StuI fragment of CBG mutant #6 | Product (Gln238/Gln347) —→ site directed mutagenesis —→ Product A (Gln238/Gln308/Gln347) |
| B. | ApaI/XbaI-restricted pSelect/CBG mutant #5 | ApaI/XbaI fragment of CBG mutant #2 | Product B (Gln9/Gln154) |
| C. | HindIII/StuI-restricted pSelect/product A | HindIII/StuI fragment of product B | Mutant #12 (Gln9/Gln154/ Gln308/Gln347) —→ |
| 13 | SalI/XbaI-restricted pSelect/product B | SalI/XbaI fragment of product A | Mutant #13 (Gln9/Gln154/Gln238/ Gln308/Gln347) —→ site directed mutagenesis —→ |
| 15 | | | Mutant #15 (Gln9/Gln74/Gln154/ Gln238/Gln308/Gln347) |
| 14. | HindIII/SalI-restricted pSelect/CBG mutant #12 | HindIII/SalI fragment of CBG mutant #15 | Mutant #14 (Gln9/Gln74/Gln154/ Gln308/Gln347) |

*CBG mutant #'s correspond to mutant #'s in Fig. 2b.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 1423 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 36..1253

( i x ) FEATURE:
( A ) NAME/KEY: sigpeptide
( B ) LOCATION: 36..101

( i x ) FEATURE:
( A ) NAME/KEY: matpeptide
( B ) LOCATION: 102..1253

( x i ) SEQUENCE DESCRIPTION: SEQ ID NO:1:

```
CAGCCTACCG CAGACTGGCC TGGCTATACT GGACA ATG CCA CTC CTC CTC TAC          53
                                       Met Pro Leu Leu Leu Tyr
                                       -22     -20

ACC TGT CTT CTC TGG CTG CCC ACC AGC GGC CTC TGG ACC GTC CAG GCC        101
Thr Cys Leu Leu Trp Leu Pro Thr Ser Gly Leu Trp Thr Val Gln Ala
    -15                 -10                 -5

ATG GAT CCT AAC GCT GCT TAT GTG AAC ATG AGT AAC CAT CAC CGG GGC        149
Met Asp Pro Asn Ala Ala Tyr Val Asn Met Ser Asn His His Arg Gly
  1               5                  10                  15

CTG GCT TCA GCC AAC GTT GAC TTT GCC TTC AGC CTG TAT AAG CAC CTA        197
Leu Ala Ser Ala Asn Val Asp Phe Ala Phe Ser Leu Tyr Lys His Leu
            20                  25                  30

GTG GCC TTG AGT CCC AAA AAG AAC ATT TTC ATC TCC CCT GTG AGC ATC        245
Val Ala Leu Ser Pro Lys Lys Asn Ile Phe Ile Ser Pro Val Ser Ile
        35                  40                  45

TCC ATG GCC TTA GCT ATG CTG TCC CTG GGC ACC TGT GGC CAC ACA CGG        293
Ser Met Ala Leu Ala Met Leu Ser Leu Gly Thr Cys Gly His Thr Arg
    50                  55                  60

GCC CAG CTT CTC CAG GGC CTG GGT TTC AAC CTC ACT GAG AGG TCT GAG        341
Ala Gln Leu Leu Gln Gly Leu Gly Phe Asn Leu Thr Glu Arg Ser Glu
 65                  70                  75                  80

ACT GAG ATC CAC CAG GGT TTC CAG CAC CTG CAC CAA CTC TTT GCA AAG        389
Thr Glu Ile His Gln Gly Phe Gln His Leu His Gln Leu Phe Ala Lys
```

| | | | | | | | | | | | | | | | | |
|---|---|---|---|---|---|---|---|---|---|---|---|---|---|---|---|---|
| TCA | GAC | ACC | AGC | TTA | GAA | ATG | ACT | ATG | GGC | AAT | GCC | TTG | TTT | CTT | GAT | 437 |
| Ser | Asp | Thr | Ser 100 | Leu | Glu | Met | Thr | Met 105 | Gly | Asn | Ala | Leu | Phe 110 | Leu | Asp | |
| GGC | AGC | CTG | GAG | TTG | CTG | GAG | TCA | TTC | TCA | GCA | GAC | ATC | AAG | CAC | TAC | 485 |
| Gly | Ser | Leu 115 | Glu | Leu | Leu | Glu | Ser 120 | Phe | Ser | Ala | Asp | Ile 125 | Lys | His | Tyr | |
| TAT | GAG | TCA | GAG | GTC | TTG | GCT | ATG | AAT | TTC | CAG | GAC | TGG | GCA | ACA | GCC | 533 |
| Tyr | Glu 130 | Ser | Glu | Val | Leu | Ala 135 | Met | Asn | Phe | Gln | Asp 140 | Trp | Ala | Thr | Ala | |
| AGC | AGA | CAG | ATC | AAC | AGC | TAT | GTC | AAG | AAT | AAG | ACA | CAG | GGG | AAA | ATT | 581 |
| Ser 145 | Arg | Gln | Ile | Asn | Ser 150 | Tyr | Val | Lys | Asn | Lys 155 | Thr | Gln | Gly | Lys | Ile 160 | |
| GTC | GAC | TTG | TTT | TCA | GGG | CTG | GAT | AGC | CCA | GCC | ATC | CTC | GTC | CTG | GTC | 629 |
| Val | Asp | Leu | Phe | Ser 165 | Gly | Leu | Asp | Ser | Pro 170 | Ala | Ile | Leu | Val | Leu 175 | Val | |
| AAC | TAT | ATC | TTC | TTC | AAA | GGC | ACA | TGG | ACA | CAG | CCC | TTT | GAC | CTG | GCA | 677 |
| Asn | Tyr | Ile | Phe 180 | Phe | Lys | Gly | Thr | Trp 185 | Thr | Gln | Pro | Phe | Asp 190 | Leu | Ala | |
| AGC | ACC | AGG | GAG | GAG | AAC | TTC | TAT | GTG | GAC | GAG | ACA | ACT | GTG | GTG | AAG | 725 |
| Ser | Thr | Arg 195 | Glu | Glu | Asn | Phe | Tyr 200 | Val | Asp | Glu | Thr | Thr 205 | Val | Val | Lys | |
| GTG | CCC | ATG | ATG | TTG | CAG | TCG | AGC | ACC | ATC | AGT | TAC | CTT | CAT | GAC | TCA | 773 |
| Val | Pro | Met 210 | Met | Leu | Gln | Ser | Ser 215 | Thr | Ile | Ser | Tyr | Leu 220 | His | Asp | Ser | |
| GAG | CTC | CCC | TGC | CAG | CTG | GTG | CAG | ATG | AAC | TAC | GTG | GGC | AAT | GGG | ACT | 821 |
| Glu 225 | Leu | Pro | Cys | Gln | Leu 230 | Val | Gln | Met | Asn | Tyr 235 | Val | Gly | Asn | Gly | Thr 240 | |
| GTC | TTC | TTC | ATC | CTT | CCG | GAC | AAG | GGG | AAG | ATG | AAC | ACA | GTC | ATC | GCT | 869 |
| Val | Phe | Phe | Ile | Leu 245 | Pro | Asp | Lys | Gly | Lys 250 | Met | Asn | Thr | Val | Ile 255 | Ala | |
| GCA | CTG | AGC | CGG | GAC | ACG | ATT | AAC | AGG | TGG | TCC | GCA | GGC | CTG | ACC | AGC | 917 |
| Ala | Leu | Ser | Arg 260 | Asp | Thr | Ile | Asn | Arg 265 | Trp | Ser | Ala | Gly | Leu 270 | Thr | Ser | |
| AGC | CAG | GTG | GAC | CTG | TAC | ATT | CCA | AAG | GTC | ACC | ATC | TCT | GGA | GTC | TAT | 965 |
| Ser | Gln | Val 275 | Asp | Leu | Tyr | Ile | Pro 280 | Lys | Val | Thr | Ile | Ser 285 | Gly | Val | Tyr | |
| GAC | CTT | GGA | GAT | GTG | CTG | GAG | GAA | ATG | GGC | ATT | GCA | GAC | TTG | TTC | ACC | 1013 |
| Asp | Leu | Gly | Asp 290 | Val | Leu | Glu | Glu | Met 295 | Gly | Ile | Ala | Asp | Leu 300 | Phe | Thr | |
| AAC | CAG | GCA | AAT | TTC | TCA | CGC | ATC | ACC | CAG | GAC | GCC | CAG | CTG | AAG | TCA | 1061 |
| Asn | Gln | Ala | Asn | Phe 305 | Ser | Arg | Ile | Thr | Gln 310 | Asp | Ala | Gln | Leu | Lys 315 | Ser | |
| | | | | | | | | | | | | | | | | 320 |
| TCA | AAG | GTG | GTC | CAT | AAA | GCT | GTG | CTG | CAA | CTC | AAT | GAG | GAG | GGT | GTG | 1109 |
| Ser | Lys | Val | Val | His 325 | Lys | Ala | Val | Leu | Gln 330 | Leu | Asn | Glu | Glu | Gly 335 | Val | |
| GAC | ACA | GCT | GGC | TCC | ACT | GGG | GTC | ACC | CTA | AAC | CTG | ACG | TCC | AAG | CCT | 1157 |
| Asp | Thr | Ala | Gly 340 | Ser | Thr | Gly | Val | Thr 345 | Leu | Asn | Leu | Thr | Ser 350 | Lys | Pro | |
| ATC | ATC | TTG | CGT | TTC | AAC | CAG | CCC | TTC | ATC | ATC | ATG | ATC | TTC | GAC | CAC | 1205 |
| Ile | Ile | Leu 355 | Arg | Phe | Asn | Gln | Pro 360 | Phe | Ile | Ile | Met | Ile 365 | Phe | Asp | His | |
| TTC | ACC | TGG | AGC | AGC | CTT | TTC | CTG | GCG | AGG | GTT | ATG | AAC | CCA | GTG | TAAGAGAC | 1260 |
| Phe | Thr | Trp 370 | Ser | Ser | Leu | Phe 375 | Leu | Ala | Arg | Val | Met 380 | Asn | Pro | Val | | |

| | | | | |
|---|---|---|---|---|
| CCCACCCAGA | GCCTCAGCAC | TGTCTGACTT | TGGGAACCAG | GGATCCCACA | GAAATGTTTT | 1320 |
| GGAGAGCGGG | AGGTTTCCCC | CAATCTCCTC | CAAGTTCTTC | TCCCTCCAAC | CAGAGTTGTG | 1380 |
| TCTAACTTTA | GGCATCTTTT | AATAAATGTC | ATTGCGACTC | TGA | | 1423 |

( 2 ) INFORMATION FOR SEQ ID NO:2:

(i) SEQUENCE CHARACTERISTICS:
  (A) LENGTH: 405 amino acids
  (B) TYPE: amino acid
  (D) TOPOLOGY: linear (ii) MOLECULE TYPE: protein (xi) SEQUENCE DESCRIPTION: SEQ ID NO:2:

```
Met  Pro  Leu  Leu  Leu  Tyr  Thr  Cys  Leu  Leu  Trp  Leu  Pro  Thr  Ser  Gly
-22       -20                      -15                      -10

Leu  Trp  Thr  Val  Gln  Ala  Met  Asp  Pro  Asn  Ala  Ala  Tyr  Val  Asn  Met
     -5                      1                   5                            10

Ser  Asn  His  His  Arg  Gly  Leu  Ala  Ser  Ala  Asn  Val  Asp  Phe  Ala  Phe
               15                       20                            25

Ser  Leu  Tyr  Lys  His  Leu  Val  Ala  Leu  Ser  Pro  Lys  Lys  Asn  Ile  Phe
               30                       35                            40

Ile  Ser  Pro  Val  Ser  Ile  Ser  Met  Ala  Leu  Ala  Met  Leu  Ser  Leu  Gly
               45                       50                            55

Thr  Cys  Gly  His  Thr  Arg  Ala  Gln  Leu  Leu  Gln  Gly  Leu  Gly  Phe  Asn
     60                       65                       70

Leu  Thr  Glu  Arg  Ser  Glu  Thr  Glu  Ile  His  Gln  Gly  Phe  Gln  His  Leu
75                       80                       85                            90

His  Gln  Leu  Phe  Ala  Lys  Ser  Asp  Thr  Ser  Leu  Glu  Met  Thr  Met  Gly
                    95                       100                      105

Asn  Ala  Leu  Phe  Leu  Asp  Gly  Ser  Leu  Glu  Leu  Leu  Glu  Ser  Phe  Ser
               110                      115                      120

Ala  Asp  Ile  Lys  His  Tyr  Tyr  Glu  Ser  Glu  Val  Leu  Ala  Met  Asn  Phe
          125                      130                      135

Gln  Asp  Trp  Ala  Thr  Ala  Ser  Arg  Gln  Ile  Asn  Ser  Tyr  Val  Lys  Asn
     140                      145                      150

Lys  Thr  Gln  Gly  Lys  Ile  Val  Asp  Leu  Phe  Ser  Gly  Leu  Asp  Ser  Pro
155                      160                      165                      170

Ala  Ile  Leu  Val  Leu  Val  Asn  Tyr  Ile  Phe  Phe  Lys  Gly  Thr  Trp  Thr
               175                      180                      185

Gln  Pro  Phe  Asp  Leu  Ala  Ser  Thr  Arg  Glu  Glu  Asn  Phe  Tyr  Val  Asp
          190                      195                      200

Glu  Thr  Thr  Val  Val  Lys  Val  Pro  Met  Met  Leu  Gln  Ser  Ser  Thr  Ile
     205                      210                      215

Ser  Tyr  Leu  His  Asp  Ser  Glu  Leu  Pro  Cys  Gln  Leu  Val  Gln  Met  Asn
     220                      225                      230

Tyr  Val  Gly  Asn  Gly  Thr  Val  Phe  Phe  Ile  Leu  Pro  Asp  Lys  Gly  Lys
235                      240                      245                      250

Met  Asn  Thr  Val  Ile  Ala  Ala  Leu  Ser  Arg  Asp  Thr  Ile  Asn  Arg  Trp
               255                      260                      265

Ser  Ala  Gly  Leu  Thr  Ser  Ser  Gln  Val  Asp  Leu  Tyr  Ile  Pro  Lys  Val
               270                      275                      280

Thr  Ile  Ser  Gly  Val  Tyr  Asp  Leu  Gly  Asp  Val  Leu  Glu  Glu  Met  Gly
          285                      290                      295

Ile  Ala  Asp  Leu  Phe  Thr  Asn  Gln  Ala  Asn  Phe  Ser  Arg  Ile  Thr  Gln
     300                      305                      310

Asp  Ala  Gln  Leu  Lys  Ser  Ser  Lys  Val  Val  His  Lys  Ala  Val  Leu  Gln
315                      320                      325                      330

Leu  Asn  Glu  Glu  Gly  Val  Asp  Thr  Ala  Gly  Ser  Thr  Gly  Val  Thr  Leu
               335                      340                      345

Asn  Leu  Thr  Ser  Lys  Pro  Ile  Ile  Leu  Arg  Phe  Asn  Gln  Pro  Phe  Ile
               350                      355                      360
```

| Ile | Met | Ile | Phe | Asp | His | Phe | Thr | Trp | Ser | Ser | Leu | Phe | Leu | Ala | Arg |
|---|---|---|---|---|---|---|---|---|---|---|---|---|---|---|---|
| | | 365 | | | | | 370 | | | | | 375 | | | |

Val Met Asn Pro Val
     380

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

GGTTACTCAT TTGCACATAA GCT                                                      23

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:4:

CTCACTGAGT TGGAAACCCA G                                                         21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

GACCTCTCAG CGAGGTTGAA A                                                         21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

CTGTGTCTTC TGCTTGACAT A                                                         21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:7:

GACAGTCCCC TGGCCCACGT A                                                         21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

AAGAAGACAG CCCCATTGCC C    21

(2) INFORMATION FOR SEQ ID NO:9:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:9:

GCGTGAGAAC TGTGCCTGGT T    21

(2) INFORMATION FOR SEQ ID NO:10:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:10:

GGACGTCAGT TGTAGGGTGA C    21

DNA ENCODING VARIANTS OF HUMAN CORTICOSTEROID BINDING GLOBULIN

FIELD OF THE INVENTION

The present invention relates to corticosteroid binding globulin. In particular, the present invention relates to variants of corticosteroid binding globulin, their production via recombinant DNA-based techniques and their use in the treatment of inflammation.

BACKGROUND OF THE INVENTION

Corticosteroid binding globulin, hereinafter referred to as "CBG", is a plasma glycoprotein having a high affinity for endogenous glucocorticoids. CBG functions to regulate the biological activity of glucocorticoids in vivo. The binding of glucocorticoids to CBG is believed to reduce the metabolic clearance rate of glucocorticoids from plasma, thereby increasing their biological half-life. Many glucocorticoids such as steroid hormones exhibit anti-inflammatory properties. Upon binding with CBG, glucocorticoids become biologically inactivated and, thus, do not exert anti-inflammatory action. However, at sites of inflammation where glucocorticoid activity is required, glucocorticoids are enzymatically released from their CBG-bound form to assume their free active form in which they function in the capacity of an anti-inflammatory agent.

As a result of its high affinity for steroid hormones and its function in the transport of bound steroids to sites of inflammation, CBG has been found to be useful in the therapeutic treatment of inflammation by serving as a vehicle for the delivery of anti-inflammatory agents to sites of inflammation in mammals. This use has been described in U.S. Pat. Nos. 4,997,814 and 5,086,039, both of which are incorporated herein by reference.

CBG is subject to N-linked glycosylation, a common post-translational modification of proteins in eucaryotic cells. Native human CBG is highly glycosylated and carbohydrates have been reported to comprise approximately 25% of the total molecular weight of CBG (Akhrem et al., Biochim. Biophys. Acta, 1982, 714:177). Such extensive glycosylation leads to considerable size heterogeneity in native CBG. The heterogeneity of CBG results not only from the variation apt to occur in its glycosylation pattern but also the variability in the oligosaccharides binding to the various sites of glycosylation. Size heterogeneity is a feature that is undesirable with regard to the approval of CBG as a pharmaceutical because CBG is not presented as a conclusively defined product. Moreover, a composition comprising CBG may be deemed to be impure due to the variability in the constitution of CBG.

Deglycosylation of CBG appears to be an inappropriate route by which to render a fully defined CBG product as the biological activity of CBG is regulated, at least in part, by its glycosylated sites. Glycosylation is believed to regulate blood levels of CBG (Hossner et al., Endocrinology, 1981, 108:1780). Glycosylation also appears to be essential in retaining the conformation of active CBG i.e. the tertiary structure of CBG (Ghose-Dastidar et al., Proc. Natl. Acad. Sci. U.S.A., 1991, 88:6408). Further, glycosylation appears to contribute to the molecular and cellular recognition of CBG (Rosner, Endocrine Rev., 1990, 11:65, Ster'chyonok et al., J. Steroid Biochem. Molec. Biol., 1991, 40:795). Although deglycosylation of CBG has been reported not to affect the biological activity of CBG (Mickelson et al. Biochemistry, 1982, 21:654), it was acknowledged at the time that the exoglycosidases utilized in the deglycosylation did not completely remove the carbohydrates attached at all sites of glycosylation.

In accordance with the standards required to obtain approval of CBG as a pharmaceutical, it would be desirable to eliminate components of native glycosylated CBG which are superfluous to its use in the treatment of inflammation. In so doing, a more appropriate CBG product may be provided for pharmaceutical application which is homogeneous in nature and the constitution of which is more thoroughly defined.

SUMMARY OF THE INVENTION

It is an object of the present invention to provide a novel variant of corticosteroid-binding globulin which is useful in the treatment of inflammation, and a pharmaceutical composition comprising said variant.

It is a further object of the present invention to provide a method for making such a novel variant of corticosteroid-binding globulin.

Accordingly, in one aspect of the present invention there is provided a steroid-binding variant of human corticosteroid binding globulin in which at least one glycosylation site other than the glycosylation site at amino acid position 238 is functionally disrupted.

In another aspect of the present invention there is provided a pharmaceutical composition useful in treating inflammation in a mammal, said composition comprising a steroid-binding variant of human corticosteroid binding globulin in which at least one glycosylation site other than the glycosylation site at amino acid position 238 is functionally disrupted, an anti-inflammatory agent which binds with said variant, and at least one pharmaceutically acceptable adjuvant.

In another aspect of the present invention, there is provided a method for treating inflammation in a mammal comprising the step of administering to said mammal a therapeutically effective amount of a pharmaceutical composition comprising a steroid-binding variant of human corticosteroid binding globulin in which at least one glycosylation site other than the glycosylation site at amino acid position 238 is functionally disrupted, an anti-inflammatory agent which binds with said variant, and at least one pharmaceutically acceptable adjuvant.

In a further aspect of the present invention there is provided a DNA molecule encoding a steroid-binding variant of human corticosteroid binding globulin in which at least one glycosylation site other than the glycosylation site at amino acid position 238 is functionally disrupted.

In a further aspect of the present invention there is provided a host cell having incorporated expressibly therein a DNA molecule encoding a steroid-binding variant of human corticosteroid binding globulin in which at least one glycosylation site other than the glycosylation site at amino acid position 238 is functionally disrupted.

In a further aspect of the present invention there is provided a method for producing a steroid-binding variant of human corticosteroid binding globulin in which at least one glycosylation site other than the glycosylation site at amino acid position 238 is functionally disrupted, comprising the step of culturing host cells having incorporated expressibly therein DNA encoding said steroid-binding variant.

BRIEF REFERENCE TO THE DRAWINGS

Embodiments of the present invention will be described by way of example by reference to the following figures in which:

FIGS. 1a and 1b illustrate the nucleotide sequence (SEQ ID NO: 1) of a cDNA molecule isolated from a lambda gt11 human liver cDNA library, and the deduced amino acid sequence (SEQ ID NO: 2) of human CBG;

FIG. 2a is a table identifying the nucleotide sequences (SEQ ID NOS. 3-10) of mutagenic oligonucleotide primers used to mutate CBG DNA; FIG. 2b is a table identifying the mutated forms of CBG and indicating the yield of such recombinantly-produced mutants;

FIG. 3 is a table setting out the construction of CBG variant including two or more mutations.

DETAILED DESCRIPTION OF THE INVENTION

Figure 4:
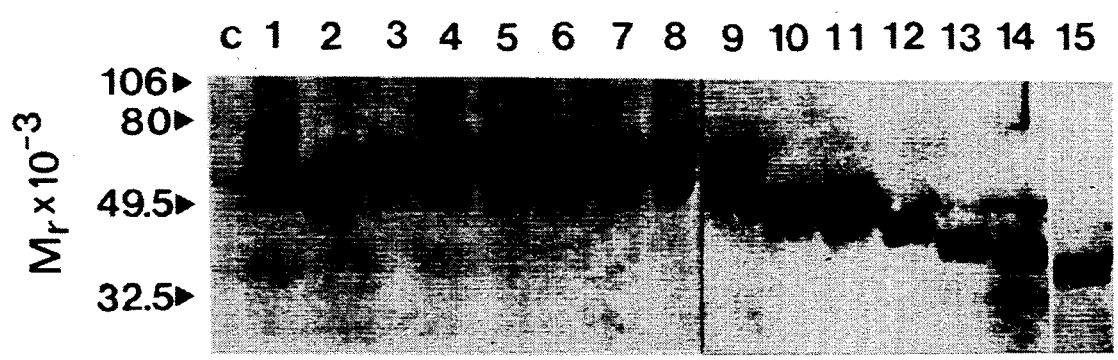
FIG. 4 illustrates the results of the SDS-PAGE analysis of the CBG variants identified in FIG. 2b.

It has been found that the binding affinity of CBG for anti-inflammatory agents is retained in a CBG variant corresponding to native human CBG which is mutated to eliminate at least one site and preferably all sites of glycosylation which are superfluous to the binding activity of CBG. Accordingly, the binding affinity of a substantially homogenous CBG variant for anti-inflammatory agents may be exploited to improve upon the utility of native CBG in the treatment of inflammation. The present steroid-binding CBG variant functions to deliver anti-inflammatory agents to sites of inflammation in a mammal by forming a CBG variant:anti-inflammatory ligand complex. Anti-inflammatory agents, such as glucocorticoids, are inactivated when bound to the CBG variant; however, the anti-inflammatory agent becomes active when released from the CBG variant by the action of the enzyme, leukocyte elastase, which is localized at sites of inflammation, allowing the agent to exert anti-inflammatory action at the inflamed site.

As used herein, the term "steroid-binding variant" is meant to encompass those variants of CBG capable of binding corticosteroids having anti-inflammatory activity, the binding of the steroid to the variant being sufficient to maintain an association therebetween, and to allow disruption of steroid binding and release of the steroid at a site of inflammation by enzymatic cleavage.

Native human CBG includes six regions defining consensus sites for the attachment of N-linked oligosaccharide chains. Specifically, these sites of glycosylation occur at amino acid positions 9, 74, 154, 238, 308 and 347 of the amino acid sequence of human CBG, the initial residue of each of which is boxed in FIGS. 1a and 1b. In terms of amino acid sequence, the consensus sites are generally defined by the sequence:

Asn—X—Thr/Ser wherein X specifically represents methionine at position 10, leucine at position 75, lysine at position 155, glycine at position 239, phenylalanine at position 309 and leucine at position 348. However, X is not particularly restricted to the amino acid that naturally exists at each consensus site and may alternatively represent any amino acid selected from the group consisting of methionine, leucine, tyrosine, threonine, cysteine, tryptophan, alanine, lysine, serine, glycine, valine, glutamine, glutamic acid, asparagine, aspartic acid, histidine, arginine, phenylalanine and isoleucine. Consensus sites altered at X maintain their capability to bind N-linked oligosaccharide chains. A consensus site may also include proline as X; however, such a substitution is undesirable as it renders glycosylation at that site unpredictable, i.e. glycosylation may or may not occur.

A single specific glycosylated site has been determined to be essential for CBG to maintain its corticosteroid binding activity, namely the glycosylation site occurring at position 238 of CBG. In native human CBG, this glycosylation site has been identified as:

$Asn^{238}$—$Gly^{239}$—$Thr^{240}$

Accordingly, in a preferred embodiment, CBG mutated to eliminate all but a single native glycosylation site at position 238, which includes asparagine at position 238, glycine at position 239 and threonine at position 240, retains an affinity for corticosteroids. This $Asn^{238}$ CBG variant is mutated to eliminate the sites of N-glycosylation occurring at amino acid positions 9, 74, 154, 308 and 347. Thus, the consensus sequences at these sites is functionally disrupted, desirably by amino acid replacement, such that glycosyl transferases no longer recognize and glycosylate at these sites. The term "functionally disrupted" as used herein with respect to the consensus sequences means altered such that the sequence does not function as a glycosylation site.

Asparagine at position 238 is essential for glycosylation to occur at site 238 and thus, is essential for corticosteroid binding. However, glycosylation at this site occurs if the amino acids at positions 239 and 240 are substituted. Specifically, glycine at position 239 may be substituted as indicated with respect to X above. Further, threonine at position 240 may be substituted with the amino acid serine. Thus, in accordance with another embodiment of the present invention, $Asn^{238}$ CBG variant mutated to eliminate all other sites of N-glycosylation and mutated further by substitution at position 239 and/or position 240 retains an affinity for corticosteroids. In general, it is preferred that CBG variants in accordance with the present invention do not include mutations in which adjacent amino acids have been altered. Variants which include adjacent mutations introduce the possibility of eliciting an immunogenic response on administration to a mammal.

The amino acid sequence of CBG is highly conserved in CBG variant according to the present invention and the binding affinity of the variant for glucocorticoid compounds is retained. The variant is, however, substantially de-glycosylated in contrast to native CBG providing a variant of CBG that exhibits substantial size homogeneity. Thus, the present invention advantageously eliminates heterogeneity to permit isolation of an active substantially homogeneous form of CBG which is useful in the treatment of inflammation.

In a further embodiment of the present invention, the corticosteroid binding affinity of the $Asn^{238}$ CBG variant may be amplified by retaining a second glycosylation site at amino acid position 74, $Asn^{74}$. This site must include asparagine at position 74 to function as a site of glycosylation and, thus, to amplify the binding affinity of the variant for glucocorticoid compounds. The amino acid at position 75 is not particularly restricted and may be leucine as in native human CBG or any one of the amino acids as defined for X above. Further, the amino acid at position 76 may be threonine as in native human CBG or, alternatively, may be serine.

The CBG variant of the present invention may be produced by any one of a number of suitable techniques based on recombinant DNA technology. It will be appreciated that such techniques are well-established by those skilled in the art, and involve the expression of CBG variant-encoding DNA in a genetically engineered host cell.

As CBG variant according to the present invention has not been found to exist in nature, DNA encoding CBG variant may be derived from CBG DNA. In view of previous reports indicating that CBG is synthesized in the liver, one method for obtaining CBG DNA includes screening a human liver cDNA library using hCBG antibody, as described herein in the examples.

DNA encoding CBG may be altered or mutated in order to encode CBG variant. One method suitable to mutate CBG DNA is known as site-directed mutagenesis, as described by Kunkel et al. in Proc. Natl. Acad. Sci., 1985, 82:488. In general terms, site-directed mutagenesis is used to alter specifically one or more amino acids in a given peptide sequence by mutating specific nucleotide bases in the DNA sequence encoding the peptide. A segment of CBG DNA encoding a portion of CBG to be mutated is cloned into a bacteriophage vector, such as an M13 bacteriophage vector. Replication of the vector in the phage results in single-stranded DNA that serves as a template for the hybridization of a primer oligonucleotide. The primer is highly complementary to the CBG DNA template while including one or more desired nucleotide base changes in its central region. The primer anneals to the single-stranded template and replication to form double-stranded DNA occurs, which ultimately yields single-stranded DNA, half of which includes native CBG DNA and the other half of which includes the mutated CBG DNA. DNA encoding mutated CBG may be selected for using any one of several selection techniques known in the art, for example, a radiolabelled oligonucleotide probe may be used for selection purposes. Upon obtaining a complete set of mutated CBG DNA segments, they may be ligated to form a DNA strand encoding CBG variant. CBG variant DNA obtained in this way may be amplified using the polymerase chain reaction (PCR) technique as disclosed by Barnett et al. in Nucl. Acids Res., 1990, 18(10):3094. Briefly, PCR is a cyclical amplification process in which the DNA sequence to be amplified is repeatedly denatured in the presence of nucleotides and DNA polymerase in order to promote replication thereof.

Alternatively, DNA encoding CBG variant may be synthesized de novo by techniques well-known in the art. This is possible due to the fact that the amino acid sequence for CBG, and thus, the DNA sequence encoding CBG are known. Accordingly, the DNA sequences encoding CBG variant will correspond to that of CBG with the exception of the base changes incorporated at those consensus glycosylation sites which may be functionally disrupted, namely those sites at positions 9, 154, 308, 347 and optionally position 74. Generally, gene synthesis may be conducted by the successive 3' to 5' coupling of appropriately protected nucleotide reagents in an automated synthesizer, followed by recovery of the deprotected polynucleotide. Alternatively, the block ligation methodology may be employed whereby oligonucleotide "blocks", including up to about 80 nucleotides, are ligated by overhang complementarity as described in Wosnick et al. in Gene, 1989, 76:153. Sequences obtained by de novo synthesis may be amplified by PCR as set out above.

The mutations effected to the sequence of CBG DNA in the preparation of CBG variant DNA are not particularly restricted providing that glucocorticoid binding affinity is retained in the resulting CBG variant. It is preferred that CBG variant DNA is mutated solely at sites encoding the amino acids in the glycosylation sites at positions 9, 74, 154, 308 and 347 of CBG in order to functionally disrupt these sites. Preferably these sites are functionally disrupted by mutation of the DNA sequence which causes replacement of the asparagine residue within each site as the asparagine residue appears to be essential to render a functional glycosylation site. The mutation effected to the DNA may be any mutation which is sufficient to replace asparagine with another amino acid. Mutations effected to the DNA may be point mutations, mutations of a single nucleotide base pair, which alter the amino acid encoded, or they may be mutations in which all the nucleotide base pairs of a codon are replaced. There is no restriction on the amino acid which replaces the asparagine residue of each glycosylation site. Thus, the codon for asparagine, AAC or AAT, may be mutated to form, for example, a glutamine codon, CAA or CAG, a lysine codon, AAA or AAG, or a glycine codon, GGA.

Upon obtaining CBG variant DNA, recombinant techniques for producing CBG variant therefrom generally involve insertion of the DNA sequence into a suitable expression vector which is subsequently introduced into an appropriate host cell for expression. Such transformed host cells are herein characterized as having the CBG variant DNA incorporated "expressibly" therein. Suitable expression vectors are those vectors which will drive expression of the inserted CBG variant DNA in the selected host. Typically, expression vectors are prepared by site-directed insertion therein of a CBG variant DNA construct. The DNA construct is prepared by replacing a coding region, or a portion thereof, with CBG variant DNA within a gene native to the selected host, or in a gene originating from a virus infectious to the host. In this way, regions required to control expression of the CBG variant DNA which are recognized by the host, including a region 5' of the CBG variant DNA to drive expression and a 3' region to terminate expression, are inherent in the DNA construct. To allow selection of host cells stably transformed with the expression vector, a selection marker is generally included in the vector which takes the form of a gene conferring some survival advantage on the transformants such as antibiotic resistance.

Expression of CBG variant DNA, for example, in yeast can be achieved using the expression-controlling regions of the yeast genes for proteins such as alcohol dehydrogenase, melibiase and many others. In Aspergillus species, CBG variant production can be driven by the regions which control the expression of alcohol dehydrogenase and aldehyde dehydrogenase in *Aspergillus nidulans*, glucoamylase in *A. niger*, and amylase in *A. oryzae*. The expression controlling regions of baculovirus genes may be utilized in insect cell-based production of CBG variant. For mammalian cell-based production of CBG variant, expression controlling regions associated with SV40 and CMV viruses are suitable for use. Further, the control regions that regulate metallothionine in mammalian cells are also suitable.

Suitable hosts for use in expressing CBG variant DNA include those hosts which are capable of glycosylating the protein product. Suitable microbial host organisms include fungi such as Aspergillus and yeast. Eukaryotic cell systems including mammalian cell systems, such as Chinese hamster ovary cells (CHO cells) for example of K1 lineage (ATCC CCL 61) including the Pro5 variant (ATCC CRL 1281); fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including HeLA lineage (ATCC CCL 2) and neuroblastoma cells of the lines IMR-32 (ATCC CCL 127), SK-N-MC (ATCC HTB 10) and SK-N-SH (ATCC HTB 11).

According to one embodiment of the present invention, mammalian CHO cells are selected to serve as host cells for the expression of CBG variant DNA. The CBG variant DNA is inserted into a pRc/CMV expression vector which is suitable to achieve mammalian cell expression of the DNA, a vector which exploits the promoter of a virus that infects CHO cells. The pRc/CMV vector comprises a pRc plasmid into which the promoter from cytomegalovirus (CMV) is cloned. CBG variant DNA is inserted into the vector at a site downstream from the CMV promoter. Specifically, HindIII and XbaI restriction sites located downstream of the promoter are digested to allow insertion of a DNA strand, which includes CBG variant-encoding DNA, the ends of which are appropriate for ligation to the HindIII and XbaI enzyme-digested ends of the vector. The CHO cells are then incubated with the CBG variant DNA-containing pRc/CMV vector under conditions which stimulate uptake of DNA. Stably transformed CHO cells are selected for by growth in a neomycin-rich medium as neomycin resistance is a property bestowed upon cells transformed with the vector.

Cells stably transformed with a CBG variant DNA-containing vector are grown in culture media and under growth conditions that facilitate the growth of the particular host cell used. One of skill in the art would be familiar with the media and other growth conditions required by the particular host cell chosen, as such information is well-documented in the art.

Recombinant CBG variant may be isolated from the host culture media by any one of a number of acceptable methods. A particularly efficient technique for isolating CBG variant includes the use of affinity columns. Ligand having a high affinity for CBG variant, such as glucocorticoid or derivatives thereof, is immobilized on the column and functions to remove CBG variant from the culture sample. Such a method is described for the isolation of CBG from serum by Rosner in J. Steroid Biochem, 1972, 3, 531–542. Further, immunogenic methods, using antibodies directed specifically to CBG variant, may be utilized in the isolation of CBG variant. In this regard, Robinson et al. (J. Endocr. (1985) 104, 259–267) describe a method used to immunogenically precipitate CBG from serum. CBG collected by the use of an affinity column, immunogenic methods, or any other suitable method for isolation, may be purified using techniques also well-known in the art such as gel electrophoresis.

The method of obtaining the CBG variant is not particularly restricted provided that the CBG variant retains glucocorticoid binding affinity. Further, the complex formed by CBG variant and its anti-inflammatory ligand must be susceptible to cleavage by elastase in order that the anti-inflammatory ligand is released from CBG variant at a site of inflammation allowing it to assert anti-inflammatory activity. Thus, the function of CBG variant in the delivery and release of anti-inflammatory agents at a site of inflammation is analogous to the function of CBG in this regard. However, the CBG variant provides a substantially homogeneous delivery vehicle in contrast to the heterogeneous nature of native CBG.

According to an aspect of the invention, anti-inflammatory agents which bind with the CBG variant are administered in the form of a complex in which the anti-inflammatory agent functions as a ligand which binds to CBG variant. The binding of the anti-inflammatory agent to the CBG variant is mediated by the affinity between the CBG variant and the anti-inflammatory agent and is not a physical bonding of the two compounds.

Anti-inflammatory agents suitable for use in the present invention should be acceptable for pharmaceutical use, and include those suitable for use with CBG as described in U.S. Pat. No. 5,086,039. Particularly suitable are the natural ligands of CBG including cortisol, corticosterone and progesterone. Synthetic glucocorticoids which bind to CBG are also suitable for use with the CBG variant such as prednisolone and methylprednisolone. Other suitable anti-inflammatory agents generally include those that have a sufficient level of anti-inflammatory activity and an appropriate binding affinity for the CBG variant. Preferred anti-inflammatory agents have an affinity constant for CBG variant within the range of from about 0.1 to 10 nanomolar at about 4° C. and physiological pH. Most preferably, the binding affinity for CBG variant approximates the binding affinity of the natural cortisol ligand for CBG which is about 0.7 nanomolar at 4° C. and physiological pH as measured using the protocol set out in Mickelson et al., Biochemistry 1981, 20:6211. This same protocol may be used to determine the binding affinity of any anti-inflammatory agent, and thus, to determine the suitability of a given anti-inflammatory agent for use in the invention.

Compositions of the invention are prepared by admixture of the selected anti-inflammatory agent with the CBG variant in a solution such as physiological saline of pH 7.5. The formation of the required complex of CBG variant and anti-inflammatory agent may be facilitated by incubating at physiological temperature and pH. It is important that the pH is maintained above a pH of 6 since the affinity of CBG for glucocorticoids is substantially reduced below pH 6, and thus, it is believed that the affinity of CBG variant for glucocorticoids would also be reduced below pH 6. It is preferred that the composition be prepared with an excess of glucocorticoid in order that all of the CBG variant in the composition is complexed with glucocorticoid. In this way, the localizing effect of the CBG variant is maximized. Saturation of CBG variant in the composition may be accomplished by the addition of a stoichiometric excess of glucocorticoid such as a molar ratio of 2:1 glucocorticoid:CBG variant.

The CBG variant-anti-inflammatory agent complex may be combined with any suitable pharmaceutically acceptable adjuvant to form an administrable composition. As used herein, the expression "pharmaceutically acceptable" means acceptable for use in the pharmaceutical and veterinary arts, not being toxic or otherwise unacceptable. The selection of adjuvant depends on the intended mode of administration of the composition. Thus, compositions to be administered by injection are prepared using liquid adjuvants such as buffered saline and physiological saline. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered, for example, antimicrobial agents may be added to the composition to prevent microbial growth over prolonged storage periods.

The compositions of the invention are useful in the treatment of a variety of conditions in mammals involving inflammation, as are compositions comprising CBG. Included among the conditions treatable with the present compositions are those conditions that the anti-inflammatory agent in the complex is known to treat. Reference may be made to Pharmacopoeias such as Martindale, The Extra Pharmacopoeia Ed, J. E. F. Reynolds, The Pharmaceutical Press, London, 1982, to identify anti-inflammatory agents used to treat specific conditions.

In accordance with the invention, a therapeutically effective amount of the present composition is administered to a mammal in the treatment of inflammation. As used herein, the term "therapeutically effective amount" is an amount of the composition indicated for treatment of the inflammatory condition while not exceeding an amount which may cause adverse effects. Because the release of anti-inflammatory agent is controlled by the CBG variant, lower amounts of the present composition may be useful in the treatment of an inflammatory condition than compositions which contain anti-inflammatory agent per se. When administered systemically as an injectable solution, formulations will comprise glucocorticoid, in bound form, in a molar range of about 5–500 $\mu$M. To determine appropriate unit doses for treating specific inflammatory conditions, reference may be had to The Extra Pharmacopoeia identified in the foregoing.

Compositions of the invention are suitable for the treatment of inflammatory conditions in mammals, and thus are not limited to treating inflammation in humans. CBG has been found to be conserved as regards the glycosylation site at amino acid position 238 in several mammalian species. Accordingly, species specific CBG variant including at least the glycosylation site at position 238 may be formed which exhibits effective glucocorticoid binding affinity. Thus, CBG variants of other mammalian species may be combined with a suitable anti-inflammatory ligand for use in treating inflammation in these species.

Embodiments of the present invention are described in the following specific examples which are not to be construed as limiting.

CONSTRUCTION OF CBG VARIANT

A lambda gt11 human liver cDNA library was screened using monospecific rabbit antiserum for human CBG as described by Hammond et al., "Primary Structure of Human Corticosteroid Binding Globulin", Proc. Natl. Acad. Sci. USA, 1987, 84:5153. A cDNA clone isolated therefrom was radiolabelled ($^{32}$P-labelled dCTP) and used to rescreen the cDNA library in order to isolate a full-length CBG cDNA. Nitrocellulose filters (Schleicher and Schuell; BA85, 0.45 $\mu$m pore size) were used to transfer DNA and were hybridized with $2\times10^6$ dpm of the CBG cDNA probe per ml, in the presence of 50% (vol/vol) formamide at 42° C. Blots were washed three times for 5 min. at room temperature in 0.3M NaCl/0.03M sodium citrate ($2\times$SSC), and once for 30 min in $1\times$SSC at 42° C. Filters were autoradiographed for 24 hr with Kodak XR-5 film at $-80$° C. with a Dupont Cronex Hi-Plus intensifying screen.

Site-directed mutagenesis was conducted in order to obtain DNA encoding CBG variants. Mutagenic oligonucleotide primers having 21–23 nucleotides were synthesized. A primer complementary to a 21–23 nucleotide region of each of the six consensus sequences was formed, each including one or two altered nucleotides in a central region corresponding to the glycosylation sites at positions 9, 74, 154, 238, 308 and 347. Each of the six glycosylation sites of CBG were mutated individually using a specific mutagenic primer. The mutagenic primers each included base pair mutations to alter the codon encoding the amino acid asparagine of the consensus sequence to a codon for glutamine. Additional primers were synthesized to alter the codon for threonine at positions 76 and 240 to a codon for alanine. The sequences of each of the primers used is set out in FIG. 2a (SEQ ID Nos. 3–10). The identity of the variants obtained, specifically, mutants #2 to #15, is set out in FIG. 2b.

Isolated CBG cDNA was inserted into a HindIII/XbaI-digested pSelect-1 phagemid (obtained from Promega Corp.) HindIII and XbaI sequences were added onto the CBG cDNA using PCR. The pSelect-1 phagemid is a chimeric plasmid containing the origin of a single-stranded DNA bacteriophage. The phagemid contains a multiple cloning site in the lacZ $\alpha$-peptide encoding region allowing for white/blue colony selection and further includes both SP6 and T7 RNA polymerase promoters. The pSelect-1 phagemid carries gene sequences for both ampicillin and tetracycline resistance; however, due to a shift in the reading frame of the ampicillin gene, the plasmid is ampicillin sensitive. An ampicillin repair oligonucleotide is provided by the manufacturer which may be used to restore ampicillin resistance thereto.

Site-directed mutagenesis was carried out using the following protocol. 200 ng (0.1 pmol) single-stranded DNA (i.e. pSelect-1 phagemid containing CBG cDNA), 2.2 ng (0.25 pmol) of the ampicillin repair oligonucleotide, and 10–15 ng (approximately 1.25 pmol) of phosphorylated mutagenic primer oligonucleotide were combined to a final volume of 20 $\mu$l with annealing buffer (20 mM Tris-HCl, pH 7.5, 10 mM MgCl$_2$, 50 mM NaCl). The mixture was heated to 70° C. for 5 min and was allowed to cool slowly to room temperature (15 to 30 min). The mixture was then placed on ice and 3 $\mu$l of concentrated synthesis buffer (100 mM Tris-HCl, pH 7.5, 5 mM dNTPs, 10 mM ATP, 20 mM DTT) was added followed by 5 $\mu$l of sterile H$_2$O, 10 units of T4 DNA polymerase and 2 units of T4 DNA ligase. The mixture was incubated for 90 min at 37° C. to achieve ligation and synthesis of a variant strand. A 7 $\mu$l aliquot of this reaction mixture was used to transform BMH71-18 mut S competent cells by electroporation (2.5 kV, 4.5 msec). After incubation of the cells for 1 h at 37° C., ampicillin was added to a final concentration of 125 μg/ml and the cells were grown overnight at 37° C. with shaking.

The plasmid DNA was isolated from the cells using conventional methodology and was used to transform JM-109 cells by electroporation (2.5 kV, 4.5 msec). The cells were plated onto LB-agar plates containing 125 μg/ml ampicillin and incubated at 37° C. for 12–16 h. Four to ten colonies were picked and grown in suspension. Plasmid DNA was isolated therefrom and sequenced by the Sanger et al. sequencing method as described in Proc. Natl. Acad. Sci. U.S.A. 74, 1977, 74:5463 to confirm that the targeted mutation had occurred.

CBG variant DNA strands incorporating two or more mutations, i.e. mutants #10 to #15 in FIG. 2b, were constructed as set out in FIG. 3. Generally, fragments containing a desired mutation were enzymatically excised from mutants #1 to #9 and inserted into the appropriate restriction site in plasmid-contained mutants. For example, mutant #10 was constructed by inserting the SalI/XbaI fragment from mutant #6, which contained a functionally disrupted site at position 238 (i.e. Asn codon mutated to Gln codon), into the SalI/XbaI site of mutant #3, which contained a functionally disrupted site at position 74 (i.e. Asn codon mutated to Gln codon), to obtain mutant #10 in which both sites 74 and 238 were functionally disrupted. In the construction of mutant #12, several steps were required. Specifically, in step A, site-directed mutagenesis was required. Initially, the appropriate HindIII/StuI fragment from mutant #6 was inserted into the HindIII/StuI site of mutant #9 to render a mutant in which the sites at positions 238 and 347 were functionally disrupted. Then, in order to functionally disrupt the site at position 308, site-directed mutagenesis was conducted as described above using the mutagenic oligonucleotide primer ($Asn^{308} \rightarrow Gln$) identified in FIG. 2*a* (SEQ ID No: 9).

cDNAs mutated to encode CBG variants were subcloned into a HindIII/XbaI-digested pRc/CMV eucaryotic expression vector (obtained from Invitrogen). HindIII and XbaI sequences were added onto the CBG variant cDNAs using PCR. pRc/CMV is a eukaryotic expression vector designed for high level stable expression. The vector includes the $\beta$-lactamase gene for ampicillin selection in prokaryotes, a high copy origin of replication from pVC19, the m13 origin of replication, T7 and SP6 promoters for sense and anti-sense transcription and a multiple cloning site. DNA inserted into the multiple cloning sites are expressed from the first AUG codon following the CMV (cytomegalovirus) promoter and enhancer. The neomycin resistance gene is expressed from the SV40 early promoter. The vector also includes the bovine growth hormone polyadenylation signal for polyadenylation of mRNAs.

Chinese hamster ovary cells (CHO $pro^-$; wild type cells) were transfected with pRc/CMV plasmids containing CBG variant DNA inserts using the Polybrene-DMSO technique. In brief, this technique included incubating exponentially growing CHO cells ($5\times10^5$ cells) overnight in MEM/FCS (Minimal Essential Medium with 10% fetal calf serum). The medium was replaced with a minimal volume (340 ml) of MEM/FCS containing plasmid DNA (7.5–15 $\mu g$), followed by 5 $\mu l$ of Polybrene (Aldrich) solution (10 mg/ml sterile water). The dishes were agitated several times during the 6 hour incubation at 37° C. The DNA-Polybrene mixture was removed, and 5 ml of 30% dimethyl-sulfoxide in MEM/FCS was added for 4 min. The cells were cultured in 25 ml of MEM/FCS for 48 h. Transfected cells were selected for neomycin resistance by the addition of Geneticin, G418, a neomycin analogue (Gibco/BRL), 1.8 mg G418/ml. After 10–12 days G418 resistant colonies were trypsinized and grown to confluency in the presence of G418 for an additional 10 days. MEM/FCS medium was removed, the cells were washed twice with PBS and cultured in Dulbecco's modified Eagle medium containing 100 nM cortisol for two days prior to analysis.

A radioimmunoassay was used to determine the concentration of CBG variant in the culture media. Specifically, rabbit anti-human CBG antiserum and $^{125}I$-labelled CBG having a specific activity of 5–10 $\mu Ci/\mu g$ were used. The $^{125}I$-labelled CBG was prepared by iodination of purified human CBG with carrier-free $Na^{125}I$ (Amhersham International) as described by Fraker et al., Biochem. Biophys. Res. Commun., 1978, 80:849. Due to the high structural similarity between CBG variant and the native CBG, bound radio-labelled CBG is displaced by CBG variant until equilibrium is achieved. Displaced or free $^{125}I$-labelled CBG was precipitated by incubation with kaolin-conjugated donkey anti-rabbit secondary antibody (provided by Farmos Diagnostica) and removed by centrifugation. The concentration of CBG variant was determined using a calibration curve prepared from known CBG concentrations.

Polyacrylamide gel electrophoresis was preformed according to the teaching of Laemmli, 1970, Nature (London), 227:680–685, in the presence of sodium dodecylsulfate using 4% stacking gel and 10% resolving gel. The proteins were transferred to Hybond-ECL (Amersham) membranes by electroblotting at 150–200 mA for 2 h. The blots were blocked, incubated with the anti-human CBG antiserum (1:500 diluted), and immunoreactive proteins were visualized with ECL Western blotting analysis system according to the manufacturer's protocol (Amersham).

FIG. 4 illustrates the results of the SDS-PAGE analysis. Of particular note are the differences between the bands obtained for wild-type CBG and the bands obtained for CBG variants according to the present invention. The broad band in lane 1 was obtained for wild-type CBG. The broadness of the band indicates the heterogeneity of wild-type CBG. In contrast, the band obtained in lane 12 represents CBG variant glycosylated at positions 74 and 238, while the band obtained in lane 14 represents CBG variant glycosylated solely at position 238. Both of these bands are more concise than the broad band obtained for wild-type CBG indicating the homogeneous nature of these CBG variants.

GLUCOCORTICOID BINDING ACTIVITY OF CBG VARIANTS

The steroid binding capacity of the CBG variants in the culture media was measured by saturation analysis using as a labelled ligand [$^3H$]-cortisol (55.8 Ci/mmol) obtained from DuPont, and dextran-coated charcoal as a separation agent as described by Hammond et al. in Clin. Chim. Acta, 1983, 132:101.

Initially, samples of culture media were added to tubes of PBS containing [$^3H$]-cortisol. The mixture in the tubes was vortex mixed and incubated at room temperature for 1 h followed by a further incubation in an ice-water bath for 15 min. Dextran-coated charcoal (DCC) suspension at 0° C. (1.25 g Norit "A"(Amend Drug and Chemical Co.) and 0.125 g Dextran T-70 (AB Pharmacia) in 0.01 mol/l phosphate-buffered saline containing 0.1% gelatin, pH 7) was added to the tubes to bind excess labelled cortisol. The tubes were incubated for 10 min at 0° C. After centrifugation at 3000×g for 5 min at 4° C. to sediment the DCC, the supernatants were decanted into scintilliation counting vials containing 4 ml Aqueous Counting Scintillant (Amersham), which were capped, shaken and counted for 10 min or until 10,000 cpm had accumulated. The binding capacity of the CBG variants was calculated in nmol/L after correction for dilution and the dissociation of bound complexes during the DCC treatment (12% for CBG).

The affinity of the CBG variants for cortisol was measured using the Scatchard analysis. Prior to conducting the affinity measurement, the culture media was concentrated using *Centricon microconcentrators (Amicon). According to the method outlined in Hammond et al. supra., the affinity of the CBG variants was determined by incubating culture samples of each of the variants with 1 pmol [$^3$H]-cortisol in the presence of increasing amounts of unlabelled cortisol.

Mutation of the glycosylation site at amino acid position 238 by substitution of either asparagine at position 238 with glutamine or threonine at position 240 with alanine resulted in a complete loss of steroid-binding activity as indicated by the saturation analysis. The CBG variant glycosylated solely at this site was found to bind cortisol ($K_8 = 1.1 \times 10^8$ $M^{-1}$). An increase in steroid-binding affinity was observed when the consensus glycosylation site at position 74 was also present ($K_4 = 1.9 \times 10^8$ $M^{-1}$); however, a CBG variant glycosylated solely at position 74 only had no steroid-binding activity.

We claim:

1. A DNA molecule encoding a steroid-binding variant of human corticosteroid binding globulin in which at least one glycosylation site other than the glycosylation site at amino acid position 238 is functionally disrupted by amino acid replacement.

2. A DNA molecule encoding a steroid-binding variant as defined in claim 1, wherein said variant is glycosylated solely at amino acid position 238.

3. A DNA molecule encoding a steroid-binding variant as defined in claim 1, wherein said variant is glycosylated at amino acid position 74.

4. A host cell line having incorporated expressibly therein a DNA molecule encoding a steroid-binding variant of human corticosteroid binding globulin in which at least one glycosylation site other than the glycosylation site at amino acid position 238 is functionally disrupted, wherein said host cell is capable of glycosylating said steroid-binding variant expressed therefrom.

5. A host cell line as defined in claim 4 which is a mammalian cell.

6. A host cell line as defined in claim 5 which is a human cell.

7. A method for producing a steroid-binding variant of human corticosteroid binding globulin in which at least one glycosylation site other than the glycosylation site at amino acid position 238 is functionally disrupted by amino acid replacement, comprising the step of culturing eukaryoticc host cells having incorporated expressibly therein DNA encoding said steroid-binding variant.

* * * * *